United States Patent [19]

Cristofori et al.

[11] 4,454,145
[45] Jun. 12, 1984

[54] NICOTINATES OF ALKANEDIOLS HAVING HYPOLIPIDAEMIC ACTIVITY AND PHARMACEUTICAL COMPOSITIONS CONTAINING THEM

[75] Inventors: Manlio Cristofori; Valerio Borzatta, both of Bologna; Mauro Morotti, Marzabotto, all of Italy

[73] Assignee: Alfa Farmaceutici S.p.A., Bologna, Italy

[21] Appl. No.: 369,579

[22] Filed: Apr. 19, 1982

[30] Foreign Application Priority Data

May 6, 1981 [IT] Italy ................................ 3423 A/81

[51] Int. Cl.³ .................. A61K 31/455; C07D 213/80
[52] U.S. Cl. .................................... 424/266; 546/263
[58] Field of Search ......................... 546/263; 424/266

[56] References Cited

U.S. PATENT DOCUMENTS

| 3,637,714 | 1/1972 | Carlson et al. | 564/263 |
| 3,742,068 | 6/1973 | Moersch et al. | 568/412 |
| 3,857,884 | 12/1974 | Moersch et al. | 568/412 |
| 3,930,024 | 12/1975 | Creger | 424/212 |

FOREIGN PATENT DOCUMENTS 910762 11/1962 United Kingdom .

OTHER PUBLICATIONS

Drugs of the Future, vol. 11 (2), (1977) pp. 102–103.
Maxwell et al., Artery vol. 4 (4), (1978) pp. 303–313.
Abstracts of Papers from Clinical Pharmacology & Therapeutics, vol. 17 (2), pp. 229–230.
Abstract from Lipids, vol. 12, pp. 44–48 (1977).

*Primary Examiner*—John M. Ford
*Assistant Examiner*—Bernard Dentz
*Attorney, Agent, or Firm*—Bucknam and Archer

[57] ABSTRACT

New compounds of general formula

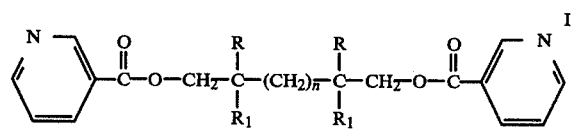

and salts therewith of pharmaceutically acceptable acids, wherein R and $R_1$ independently represent a hydrogen atom or a straight or branched alkyl group having from 1 to 5 carbon atoms, and n is an integer from 4 to 12; and of general formula

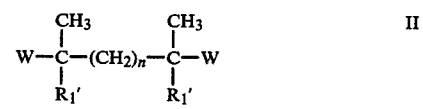

wherein $R'_1$ represents a straight or branched alkyl group having from 2 to 4 carbon atoms, W represents hydroxymethyl or the COOM group in which M stands for a hydrogen atom, an alkali metal or an equivalent of an alkali earth metal and n is an integer from 6 to 8.

9 Claims, No Drawings

NICOTINATES OF ALKANEDIOLS HAVING HYPOLIPIDAEMIC ACTIVITY AND PHARMACEUTICAL COMPOSITIONS CONTAINING THEM

BACKGROUND OF THE INVENTION

Alkanediols having serum triglyceride-lowering and serum cholesterol-lowering activity are known from U.S. Pat. No. 3,930,024. Other compounds of similar structure possessing the same biological properties were also described in U.S. Pat. Nos. 3,742,068 and 3,857,884, but alkanediols in which the hydroxy groups are esterified with nicotinic acid have never been reported in the literature. Also the compound of formula II are new.

SUMMARY OF THE INVENTION

The present invention refers to new alkanediols derivatives having hypolipidaemic activity, to methods for their preparation and to pharmaceutical compositions containing them. More exactly, the present invention refers to new compounds of general formula

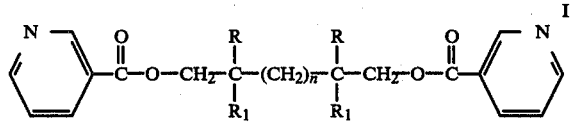

and salts therewith of pharmaceutically acceptable acids, wherein R and $R_1$ independently represent a hydrogen atom or a straight or a branched alkyl group having from 1 to 5 carbon atoms such as, for instance, methyl, ethyl, propyl, iso-propyl, n-butyl, amyl, iso-amyl, 2-methyl-2-butyl and neo-pentyl, and n represents an integer from 4 to 12.

A preferred group of compounds comprises those compounds of formula I wherein the pairs of substituents R and $R_1$ independently represent hydrogen or a straight or branched alkyl group from 1 to 5 carbon atoms and n is an integer from 6 to 8; and salts therewith of pharmaceutically acceptable acids.

A most preferred group of compounds comprises those compounds of formula I wherein the pairs of substituents R and $R_1$ independently represent methyl or ethyl, and n is an integer from 6 to 8; and salts therewith of pharmaceutically acceptable acids.

The compounds of the invention form acid addition salts with pharmaceutically acceptable acids; suitable salts include the hydrochlorides, hydrobromides, sulphates, phosphates, nitrates, acetates, propionates, succinates, adipates, glycolates, lactates, malates, ascorbates, piruvates, tartrates, maleates, citrates, bicarbonates, pamoates, phenylacetates, benzoates, salicylates, alkylsulphates, arylsulphates and glucuronates, of which the preferred salts are the hydrochlorides.

The compounds of the invention can be prepared by reacting an alkanediol of formula

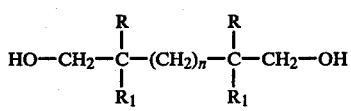

wherein R, $R_1$ and n are defined as above, with a suitable acylating agent of formula

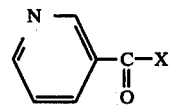

or with an acid salt thereof,
wherein X may be a halogen atom, preferably chlorine, or a suitable acyloxy residue, e.g., trifluoroacetoxy, pivaloyloxy, the group

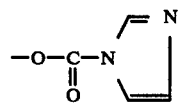

or the radical

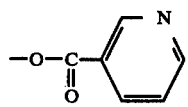

itself.

Other compounds capable of introducing the group

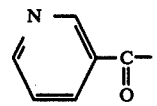

into the desired positions fall into the scopes of the present invention.

In the practice the reaction is carried out by reacting a molar amount of the compound of formula III with a molar excess of a compound of formula IV or an acid addition salt thereof. Preferably from about 4 to about 8 molar equivalent of acylating agent of formula IV or of a corresponding acid salt are employed for each molar equivalent of alkanediol of formula III. The reaction is carried out in the presence of an organic tertiary nitrogen containing base having the purpose of blocking the acidity which forms during the reaction course. This base is advantageously selected from triethylamine, dimethylaniline, quinoline, pyridine and the methylpiridines. Pyridine is preferably used, which acts also as the reaction solvent. The reaction takes place at a temperature comprised between about 50° C. and the boiling temperature of the reaction mixture, at atmospheric pressure, and is completed in an interval of time comprised between about 16 and about 48 hours. The desired compounds are recovered from reaction mixture by means of techniques which are familiar to a chemist skilled in the art. Such techniques comprises evaporating to dryness the organic solution, dissolving the residue in a suitable organic solvent like diethyl ether or dichlorometane and analogs, washing the organic phase with an aqueous solution of sodium bicarbonate or hydrochloric acid and with water and bringing again to dryness the whole.

A crystalline, amorphous or oily residue is obtained, which may further be purified by column chromatography or recrystallization from suitable solvents. Preferred crystallization solvents are ethanol and mixtures of ethanol and water.

The starting alcohols have been obtained by chemical reduction of the corresponding acids by means of suitable reducing agents, like the mixed metal hydrides as, for instance, lithium aluminum hydride, lithium aluminum hydride-aluminum chloride, aluminum hydride-aluminum chloride, sodium borohydride-aluminum chloride, in an anhydrous organic solvent such as, for instance, diethyl ether, tetrahydrofuran or dioxane, followed by an acidic or alkaline hydrolysis of the reaction complex.

A reducing system comprising lithium aluminum hydride in a mixture of anhydrous tetrahydrofuran and anhydrous diethyl ether has proved to be the preferred one. The hydrolysis is preferably carried out by adding an aqueous solution of sodium hydroxide as described in U.S. Pat. No. 3,930,024. The acids have in turn been obtained from the corresponding dinitriles, by treating a molar amount thereof with from about 8 to about 10 molar amounts of a strong alkaly agent such as, for instance, potassium hydroxide, in presence of ethylene glycol as the solvent, at a temperature corresponding to the reflux temperature of the reaction mixture, for a period of time comprised between about 16 and about 48 hours.

The dinitriles have been prepared according to the method described in U.S. Pat. No. 3,857,884.

Some of the alcohols of formula III above used as the starting materials for preparing the compounds of formula I, as well as the corresponding acids from which said alcohols derive, and, more exactly, the compounds of general formula

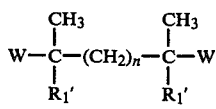

wherein $R'_1$ represents a straight or branched alkyl group having from 2 to 4 carbon atoms, W represents hydroxymethyl or the COOM group, in which M stands for a hydrogen atom, an alkali metal or an equivalent of an alkali earth metal, and n represents an integer from 6 to 8, are new and are endoved with strong hypolipidaemic properties as well.

The compounds according to the invention, more exactly the esters of formula I and the acids and alcohols of formula II, possess remarkable cholesterol and triglycerides lowering activity and moreover they display a very low toxicity, since the $LD_{50}$ values in mice are always higher than 1000 mg/Kg/os and higher than 500 mg/Kg/i.p. determined according to Irwin (Science 136, 123, 1962).

The following pharmaceutical tests have been used in order to assess the above mentioned biological properties:

(A) Determination of the decrease of triglycerides content in the serum of rats due to hypertriglyceridemia caused by fructose.
(B) Determination of the variation of total cholesterol in rats fed with Greenberg hypocholesterolemic diet modified according to Tensho et al.
(C) Determination of the decrease of triglycerides content in the serum of rats based on hypertriglyceridemia caused by ethanol.

TEST A

Male Wistar rats weighing 260±20 g, normally fed, subdivided in groups of 6 animals each, are used. The test lasts three days: in the first day the animals are normally fed but are kept without drinking water; in the second and third day they receive a 20% (w/v) water solution of fructose instead of water; moreover in the second day they are fed by means of a gastric probe with further 4 ml of 50% (w/v) aqueous solution of fructose. During the three days the animals are fed by means of a gastric probe with 50 mg/Kg/os/die of the compound to be tested. The animals are sacrificed undr ethereal anaesthesia 4 hours after the treatment of the third day and the blood is drawn by an intracardiacal injection.

The triglycerides are determined on the serum with the enzymatic method according to Eggstein, M. and Kreutz F. M., (Klin. Wschr. 44, 262, 1966).

The activity of the compounds is assessed by comparing the results obtained by the group treated both with the fructose and the compound to be tested (treated group), by the group treated only with the fructose (diet group) and by the group which has not undergone any treatment (control group). The percent decrease of the hematic triglycerides due to the treatment with the compound to be tested is expressed as $\Delta TG_{hematic}$ and is represented by the following formula:

$$\Delta TG_{hematic} = \frac{TG_{(diet\ group)} - TG_{(treated\ group)}}{TG_{(diet\ group)} - TG_{(control\ group)}} \cdot 100$$

TG = triglycerides.

TEST B

Male Wistar rats weighing 90±10 g, subdivided in groups of 10 animals each, are fed for 7 days with the Tensho et al. hypercholesterolemic diet (Acutely induced hypercholesterolemia in the rat—Yakugaku Zasshi 1972, 92, 879). The rats are subdivided in 3 experimental groups:

(1) control group, normally fed;
(2) diet group, fed only with the Tensho diet;
(3) treated group, fed with the Tensho diet and treated with the compounds to be tested.

This last group has been treated only with the hypercholesterolemic diet for the first four days, whereas in the last three days the hypercholesterolemic diet has been integrated with the treatment with the compounds of the invention. At the beginning of the eighth day the rats, fasted since the previous evenging, are sacrified under ethereal anaesthesia by means of an intracardiacal injection. The content of the serum cholesterol was determined according to D. Watson (Clin. Chim. Acta 5, 637, 1960). The percent decrease of the hematic cholesterol is calculated by means of the following formula:

$$\Delta Ch_{hematic} = \frac{Ch_{(diet\ group)} - Ch_{(treated\ group)}}{Ch_{(diet\ group)} - Ch_{(control\ group)}} \cdot 100$$

Ch = cholesterol

TEST C

Male Wistar rats weighing 260±20 g, normally fed, are subdivided in experimental groups of 10 animals each:
(1) control group, normally fed;
(2) diet group, given drinking water containing 10% (v/v) of ethanol since the second day;

(3) treated group, given drinking water containing 10% (v/v) of ethanol and treated with the compounds to be tested from the second day.

At the beginning of the fourth day, after 18 hours of fast, the animals are sacrificed under ethereal anaesthesia by means of an intracardiacal injection. The dosage of the triglycerides is carried out on the serum using the enzymatic method described by Eggstein M. and Kreutz F. M. (Klin. Wschr. 44, 262, 1966). The percent decrease of the triglycerides has been calculated as above.

The following tables report the data obtained for some representative compounds of the invention.

TABLE 1

Results of test A
General formula of the compounds:

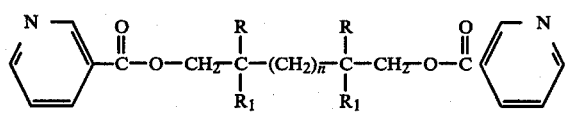

dose: 50 mg/Kg/os/die

| | R | $R_1$ | n | $\Delta TG_{hematic}$ |
|---|---|---|---|---|
| 1 | $CH_3$ | $CH_3$ | 4 | −60.0 |
| 2 | $CH_3$ | $CH_3$ | 5 | −80.0 |
| 3 | $CH_3$ | $CH_3$ | 6 | −99.0 |
| 4 | $CH_3$ | $C_2H_5$ | 6 | −87.0 |
| 5 | $CH_3$ | $n-C_3H_7$ | 6 | −90.0 |
| 6 | $CH_3$ | $n-C_4H_9$ | 6 | −85.6 |
| 7 | $CH_3$ | $CH_3$ | 7 | −92.5 |
| 8 | $CH_3$ | $C_2H_5$ | 7 | −98.0 |
| 9 | $CH_3$ | $CH_3$ | 8 | −98.0 |
| 10 | $CH_3$ | $C_2H_5$ | 8 | −66.0 |
| 11 | $CH_3$ | $n-C_3H_7$ | 8 | −65.8 |
| 12 | $CH_3$ | $n-C_4H_9$ | 8 | −59.1 |

TABLE 2

Results of test A
General formula of compounds:

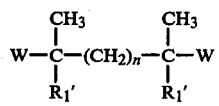

dose: 50 mg/Kg/os/die

| | W | $R_1'$ | n | $\Delta TG_{hematic}$ |
|---|---|---|---|---|
| 1 | COOH | $CH_3$ | 4 | inactive |
| 2 | $CH_2OH$ | $CH_3$ | 4 | inactive |
| 3 | COOH | $CH_3$ | 5 | inactive |
| 4 | $CH_2OH$ | $CH_3$ | 5 | inactive |
| 5 | COOH | $CH_3$ | 6 | −91.8 |
| 6 | $CH_2OH$ | $CH_3$ | 6 | −94.0 |
| 7 | COOH | $C_2H_5$ | 6 | −82.1 |
| 8 | $CH_2OH$ | $C_2H_5$ | 6 | −81.5 |
| 9 | COOH | $n-C_3H_7$ | 6 | −89.5 |
| 10 | $CH_2OH$ | $n-C_3H_7$ | 6 | −88.3 |
| 11 | COOH | $n-C_4H_9$ | 6 | −65.4 |
| 12 | $CH_2OH$ | $n-C_4H_9$ | 6 | −58.7 |
| 13 | COOH | $CH_3$ | 7 | −91.8 |
| 14 | $CH_2OH$ | $CH_3$ | 7 | −92.0 |
| 15 | COOH | $C_2H_5$ | 7 | −97.0 |
| 16 | $CH_2OH$ | $C_2H_5$ | 7 | −90.0 |
| 17 | COOH | $CH_3$ | 8 | −97.5 |
| 18 | $CH_2OH$ | $CH_3$ | 8 | −93.4 |
| 19 | COOH | $C_2H_5$ | 8 | −57.4 |
| 20 | $CH_2OH$ | $C_2H_5$ | 8 | −50.1 |
| 21 | COOH | $n-C_3H_7$ | 8 | −64.3 |
| 22 | $CH_2OH$ | $n-C_3H_7$ | 8 | −45.2 |
| 23 | COOH | $n-C_4H_9$ | 8 | −62.4 |
| 24 | $CH_2OH$ | $n-C_4H_9$ | 8 | −60.2 |

TABLE 3

Activity expressed as $ED_{50}$ values (mmole/Kg/os/die), of some representative compounds of the invention, in the three test above described

| Compound | Test diet of fructose $ED_{50}$ | Test diet of ethanol $ED_{50}$ | Test diet of Tensho $ED_{50}$ |
|---|---|---|---|
| Example 3 | 0.0034 | 0.0727 | 0.0900 |
| Example 4 | 0.0029 | 0.0718 | 0.0891 |
| Example 5 | 0.0026 | 0.0707 | 0.0880 |
| Example 1 of U.S. Pat. No. 3930024 | 0.0130 | 0.2960 | 0.8020 |
| Nicotinic acid | 0.4760 | 0.4800 | 0.3020 |

The present invention also refers to the use of the new compounds as hypocholesterolemic and hypotriglyceridemic agents, and to all of the industrially applicable acts and aspect of said use, including their embodiment into pharmaceutical compositions, which are a further specific object of the invention.

The compounds of the invention may therefore be embodied in pharmaceutical compositions suitable for oral or rectal, but preferably oral administration. For oral administration the compounds are formulated as tablets, dispersible powder, capsules, sugar coated tablets, granules, syrups, elixir or solutions. The compositions for oral use may contain one or more conventional adjuvants such as, for instance, sweetening agents, flavoring agents, coloring agents, coating and preservative agents, in order to provide an elegant and palatable preparation. Tablets may contain the active ingredient admixed with the conventional, pharmaceutically acceptable excipients, e.g. inert diluents such as calcium carbonate, sodium carbonate, lacotse and talc, granulating and disintegrating agents, such as, for instance, starch, alginic acid and sodium carboxymethylcellulose, binding agents, e.g., starch, gelatin, gum arabic and polyvinylpyrrolidone and lubricating agents, e.g., magnesium stearate, stearic acid and talc. Tablets may be coated or uncoated according to known procedures, in order to delay their disintegration and adsorption in the gastrointestinal tract and obtain "retard" compositions. Syrups, elixirs and solutions are prepared as known in the art. Together with the active ingredient they may contain suspending agents such as, for instance, methylcellulose, hydroxyethylcellulose, tragacanth and sodium alginate, wetting agents, e.g. lecithin, polyoxyethylene stearates and polyoxyethylene sorbitan monoleate, and the common preservative, sweetening and buffering agents. A capsule or a sugar coated tablet may contain the active ingredient alone or in admixture with an inert solid diluent as, for instance, calcium carbonate, calcium phosphate or kaolin.

A suppository contains the active ingredient in admixture with glycerides of saturated fatty acids or with polyethylenglycols and the usual preservative and stabilizing agents. The dosage of active ingredient useful for combatting the hypercholesterolaemia and the hypertriglyceridaemia may vary within wide limits, depending on the nature of the ingredient used. In general, good results are obtained by administering the compounds of the invention at daily dosages varying from about 3 to about 10 mg/Kg of body weight. The pharmaceutical dosage forms generally contain from 50 mg to 300 mg of active ingredient in admixture with one or more usual solid or liquid pharmaceuticals carriers and are suitable for single or multiple daily administrations.

The following examples illustrate the invention without limiting the scope of the invention itself.

EXAMPLE 1

2,2,7,7-Tetramethyl-1,8-octanediol dinicotinate

A suspension of 106.2 grams (0.6 mole) of nicotinoyl chloride hydrochloride in 300 ml of anhydrous pyridine was added in 2 hours under stirring with a solution of 20.2 grams (0.1 mole) of 2,2,7,7-tetramethyl-1,8-octanediol in 60 ml of anhydrous pyridine while keeping the temperature at about 70° C. The reaction was refluxed and stirred for 36 hours, then, after cooling, the formed precipitate was removed by filtration. The filtrate was evaporated under vacuum and the obtained residue was treated with a mixture of 200 ml of diethyl ether and 100 ml of an 8% aqueous solution of sodium bicarbonate. The organic layer was separated, washed first with 100 ml of a 3% aqueous solution of sodium bicarbonate, then with 100 ml of water and finally concentrated under vacuum to about half of the initial volume. After standing overnight, the product which separated was recovered by filtration and recrystallized from ethanol thus obtaining 22 grams of the title product, having m.p. 89°–90° C. Yield 53.4% of theoretical.

EXAMPLE 2

2,2,8,8-Tetramethyl-1,9-nonanediol dinicotinate 106.2 Grams (0.6 mole) of nicotinoyl chloride hydrochloride in 300 ml of anhydrous pyridine were reacted with 21.6 grams (0.1 mole) of 2,2,8,8-tetramethyl-1,9-nonanediol according to the procedure described in the above example.

27 Grams of title product, recrystallized from ethanol, were obtained, having m.p. 78°–79° C. Yield: 63.4% of theoretical.

EXAMPLE 3

2,2,9,9-Tetramethyl-1,10-decanediol dinicotinate 106.2 Grams (0.6 mole) of nicotinoyl chloride hydrochloride in 300 ml of anhydrous pyridine were reacted with 23.0 grams (0.1 mole) of 2,2,9,9-tetramethyl-1,10-decanediol, according to the procedure described in Example 1. 28.8 Grams of product, recrystallized from ethanol, were obtained, having m.p. 68°–69° C. Yield: 65,5% of theoretical.

EXAMPLE 4

2,2,10,10-Tetramethyl-1,11-undecanediol dinicotinate

A suspension of 53.10 grams (0.3 mole) of nicotinoyl chloride hydrochloride in 150 ml of anhydrous pyridine was added in 2 hours under stirring with a solution of 12.2 grams (0.05 mole) of 2,2,10,10-tetramethyl-1,11-undecanediol in 30 ml of anhydrous pyridine while keeping the temperature at about 70° C. The reaction was refluxed and stirred for 36 hours then, after cooling, the formed precipitate was removed by filtration. The filtrate was evaporated under vacuum and the obtained residue was treated with a mixture of 200 ml of diethyl ether and 100 ml of an 8% aqueous solution of sodium bicarbonate. The organic layer was separated and washed first with 100 of a 3% aqueous solution of sodium bicarbonate and then with 100 ml of water. After evaporating the diethyl ether in vacuo the obtained residue was dissolved in 50 ml of methylene chloride, the organic solution was twice washed with 30 ml of 1N hydrochloric acid and twice with 50 of water, dried over sodium sulphate and finally brought to dryness. The residue was crystallized from ethanol thus obtaining 11.80 grams of the title product, having m.p. 70°–71° C. Yield: 52% of theoretical.

EXAMPLE 5

2,2,11,11-Tetramethyl-1,12-dodecanediol dinicotinate 53.10 Grams (0.3 mole) of nicotinoyl chloride hydrochloride in 150 ml of anhydrous pyridine were reacted with 12.90 grams (0.05 mole) of 2,2,11,11-tetramethyl-1,12-dodecanediol according to the procedure of the above example. 11.8 Grams of the title product, recrystallized from an 80/20 (v/v) mixture of ethanol/water, were obtained, having m.p. 66°–67° C. Yield: 50.5% of theoretical.

EXAMPLE 6

According to the procedures described in the above examples, by reacting in anhydrous pyridine the nicotinoyl chloride hydrochloride with the hereinbelow listed alkanediols:

1,10-decanediol, m.p. 55°–57° C.;
2,9-diethyl-2,9-dimethyl-1,10-decanediol, oil;
2,9-dimethyl-2,9-di-n-propyl-1,10-decanediol oil;
2,9-di-n-butyl-2,9-dimethyl-1,10-decanediol, oil;
1,11-undecanediol, m.p. 38°–40° C.;
2,10-diethyl-2,10-dimethyl-1,11-undecanediol, oil;
2,9-dimethyl-2,10-di-n-propyl-1,11-undecanediol, oil;
1,12-dodecanediol, m.p. 57°–58° C.;
2,11-diethyl-2,11-dimethyl-1,12-dodecanediol, oil;
2,11-dimethyl-2,11-di-n-propyl-1,12-dodecanediol, oil;
2,11-di-n-butyl-2,11-dimethyl-1,12-dodecanediol, oil;
1,13-tridecanediol, m.p. 61°–62° C.;
1,14-tetradecanediol, m.p. 78°–79° C.;
1,15-pentadecanediol, m.p. 74°–75° C.;
1,16-hexadecanediol, m.p. 84°–85° C.;
the following dinicotinate were obtained:
1,10-decanediol dinicotinate, m.p. 51°–53° C.;
2,9-diethyl-2,9-dimethyl-1,10-decanediol dinicotinate, oil;
2,9-dimethyl-2,9-di-n-propyl-1,10-decanediol dinicotinate, oil;
2,9-di-n-butyl-2,9-dimethyl-1,10-decanediol dinicotinate, oil;
1,11-undecanediol dinicotinate dihydrochloride, m.p. 135°–137° C.;
2,10-diethyl-2,10-dimethyl-1,11-undecanediol dinicotinate, oil;
2,10-dimethyl-2,10-di-n-propyl-1,11-undecanediol dinicotinate, oil;
2,10-di-n-butyl-2,10-dimethyl-1,11-undecanediol dinicotinate, oil;
1,12-dodecanediol dinicotinate, m.p. 65°–66° C.;
2,11-diethyl-2,11-dimethyl-1,12-dodecanediol dinicotinate, oil;
2,11-dimethyl-2,11-di-n-propyl-1,12-dodecanediol dinicotinate, oil;
2,11-di-n-butyl-2,11-dimethyl-1,12-dodecanediol dinicotinate, oil;
1,13-tridecanediol dinicotinate, m.p. 52°–53° C.;
1,14-tetradecanediol dinicotinate, m.p. 75°–76° C.;
1,15-pentadecanediol dinicotinate, m.p. 61°–62° C.;
1,16-hexadecanediol dinicotinate, m.p. 80°–81° C.

In the same way the dinicotinates deriving from the following alkanediols can be prepared:
2,9-diisopropyl-2,9-dimethyl-1,10-decanediol;
2,10-diisopropyl-2,10-dimethyl-1,11-undecanediol;
2,11-diisopropyl-2,11-dimethyl-1,12-dodecanediol.

EXAMPLE 7

2,9-Diethyl-2,9-dimethyl-1,10-decanedioic acid (A) A solution of 17 ml (0.1204 mole) of diisopropylamine in 70 ml of anhydrous tetrahydrofuran was added under stirring with 60.2 ml (0.1204 mole) of a 2M solution of n-butyl-lithium in n-hexane, keeping the temperature at about 0° C. by means of an external cooling. The resulting mixture was first added, after 10 minutes, with 10.0 grams (0.1204 mole) of 2-methyl-butyronitrile and after 30 minutes with 9.6 ml (0.0602 mole) of 1,6-dibromo-hexane, keeping the temperature between 0° C. and 10° C. for one hour. After bringing to room temperature and heating for 16 hours at 35° C., the reaction solution was slowly cooled to 5°–10° C. and added with 75 ml of water. The organic layer was separated; the aqueous layer was twice extracted with diethyl ether and the ether extracts were added to the organic layer.

The resulting organic phase was washed with a saturated aqueous solution of sodium chloride, dried over anhydrous sodium sulphate, filtered and evaporated to dryness under vacuum. 14.0 Grams of 3,10-dicyano-3,10-dimethyl-dodecane were obtained, as an oily compound; yield 93.8% of theoretical.

The compound was used without any further purification for the subsequent reaction.

(B) 4.55 Grams (0.0183 mole) of the compound prepared according to step (A) were refluxed under stirring for 16 hours in 25 ml of ethylene glycol containing 10.24 grams (0.183 mole) of potassium hydroxide. After cooling and diluting with 35 ml of water, the mixture was twice washed with diethyl ether and then acifidied, under cooling, with concentrated hydrochloric acid. The reaction solution was twice extracted with diethyl ether, the ether extracts washed with water, dried over anhydrous sodium sulphate and evaporated to dryness under vacuum. A residue was obtained, which was taken up with light petroleum and recovered by filtration. Yield: 3.4 grams of 2,9-diethyl-2,9-dimethyl-1,10)decanedioic acid (65.3% of theoretical). M.p. 117°–118° C.

EXAMPLE 8

2,9-Diethyl-2,9-dimethyl-1,10-decanediol

A suspension of 1.6 grams (0.0425 mole) of lithium aluminum hydride in 40 ml of anhydrous diethyl ether was added, under vigorous stirring, with a solution of 4.87 grams (0.0170 mole) of 2,9-diethyl-2,9-dimethyl-1,10-decanedioic acid, and the resulting mixture was refluxed for 1 hour. After cooling to room temperature, the suspension was added with 12 ml of a 25% (v/v) aqueous solution of sulphuric acid. The obtained precipitate was removed by filtration and the filtrate was poured into 50 ml of a 20% aqueous solution of sodium carbonate under cooling and stirring. The organic layer was separated, washed with water, dried over anhydrous sodium sulphate and evaporated to dryness under vacuum. 4.0 Grams (90.5% of theoretical) of the chromatographycally pure title compound were obtained.

The alkanediols listed in Example 6 have been synthesized according to the procedure of Example 8.

EXAMPLE 9

A sugar coated tablet was prepared with:

| | |
|---|---|
| 2,2,9,9-Tetramethyl-1-1,10-decanediol dinicotinate | 200 mg |
| sodium carboxymethylcellulose | 10 mg |
| magnesium stearate | 10 mg |
| gelatin | 15 mg |
| saccharose | 30 mg | gum arabic, lactose, titanium dioxide, aluminum lac, according to conventional procedures.

EXAMPLE 10

A capsule was prepared with:

| | |
|---|---|
| 2,2,11,11-Tetramethyl-1,12-dodecanediol dinicotinate | 150 mg |
| talc | 20 mg |
| lactose | 20 mg |
| sodium carboxymethylcelulose | 20 mg |
| starch | 90 mg |

EXAMPLE 11

A tablet was prepared with:

| | |
|---|---|
| 2,2,9,9-Tetramethyl-1,10-decanediol dinicotinate | 150 mg |
| levilite | 50 mg |
| starch | 50 mg |
| magesium stearate | 30 mg |

We claim:

1. A derivative of an alkanediol having hypolipidemic activity of formula

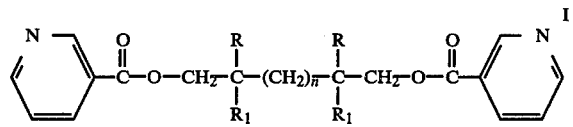

wherein the pairs of substituents R and $R_1$ independently represent methyl or ethyl and n is an integer from 6 to 8; and salts thereof with a pharmaceutically acceptable acid.

2. A compound as defined in claim 1, which is 2,2,9,9-tetramethyl-1,10-decanediol dinicotinate.

3. A compound as defined in claim 1, which is 2,2,10,10-tetramethyl-1,11-undecanediol dinicotinate.

4. A compound as defined in claim 1, which is 2,2,11,11-tetramethyl-1,12-dodecanediol dinicotinate.

5. A pharmaceutical composition useful for treating hyperlipidaemia, in unit dosage form containing as the active ingredient from about 50 to about 300 mg per unit dose of a compound as defined in claim 1 in admixture with one or more pharmaceutically acceptable carriers.

6. A pharmaceutical composition as defined in claim 5 wherein the active ingredient is 2,2,9,9-tetramethyl-1,10-decanediol dinicotinate.

7. A pharmaceutical composition as defined in claim 5 wherein the active ingredient is 2,2,10,10-tetramethyl-1,11-undecanediol dinicotinate.

8. A pharmaceutical composition as defined in claim 5 wherein the active ingredient is 2,2,11,11-tetramethyl-1,12-dodecanediol dinicotinate.

9. A method of treating hyperlipidaemia, which comprises administering to warm blooded animals, including humans, a daily dosage varying from about 3 to about 10 mg/Kg of body weight of a compound as defined in claim 1.

* * * * *